United States Patent [19]
Monter

[11] 3,946,730
[45] Mar. 30, 1976

[54] BIOMEDICAL ELECTRODE ASSEMBLY

[75] Inventor: Robert Paul Monter, Centerville, Ohio

[73] Assignee: NDM Corporation, Dayton, Ohio

[22] Filed: Jan. 21, 1972

[21] Appl. No.: 219,686

[52] U.S. Cl. ........ 128/2.06 E; 128/417; 128/DIG. 4
[51] Int. Cl.$^2$ ............................................. A61B 5/04
[58] Field of Search ............ 128/2.06 E, 2.1 E, 417, 128/418, DIG. 4; 252/518, 521

[56] References Cited
UNITED STATES PATENTS

| | | | |
|---|---|---|---|
| 2,895,479 | 7/1959 | Lloyd | 128/2.06 E |
| 3,027,333 | 3/1962 | Friedman | 128/417 |
| 3,048,549 | 8/1962 | Adams | 128/417 |
| 3,170,459 | 2/1965 | Phipps et al. | 128/2.06 E |
| 3,464,404 | 9/1969 | Mason | 128/2.06 E |
| 3,487,827 | 1/1970 | Edmark | 128/2.06 E |
| 3,701,346 | 10/1972 | Patrick, Jr. et al. | 128/2.06 E |

*Primary Examiner*—William E. Kamm
*Attorney, Agent, or Firm*—Irons & Sears

[57] ABSTRACT

A body electrode suitable for sensing bioelectrical potentials and adapted to be electrically connected to an external electrically responsive member, the body electrode including a stainless steel electrode and an aqueous alkali metal sulfate electrolyte; and methods of accurately receiving and transmitting for monitoring and diagnostic purposes small electrical voltages generated in the body.

12 Claims, 3 Drawing Figures

BIOMEDICAL ELECTRODE ASSEMBLY

BACKGROUND OF THE INVENTION

While biomedical instrumentation experts have long appreciated the diagnostic and monitoring value of bioelectrical potentials originating from, for example, the heart of a patient victimized by a myocardial infarction, accurately receiving, transmitting and recording the small voltages involved has never been an easy matter. Clinicians, general practitioners and specialists are all very much aware of the frustrations attending faulty recordings caused by motion artifacts, spurious electrical signals, corrosion, poor electrolyte stability, high skin impedance, and the like.

What with man now taxing his strength and endurance more and more at supersonic speeds, in aerospace explorations and in excursions to ocean depths, significantly increased reliance is placed on monitoring equipment and under greatly differing conditions. It is getting more important, for example, to provide electrodes which are versatile and reliable and which may be used almost as effectively with an active subject as with an immobilized person. Not only must the electrode fastened to the subjects's body be firmly secured for proper and accurate functioning, but it is necessary that the quantity of interposed electrolyte be such that it uniformly coats a predetermined area of the skin. Furthermore, this uniformity must be maintained throughout the recordings.

Also, both the comfort of the subject and the avoidance of distortions in, for example, electrocardiograms require that the electrolyte or electrode assembly should not irritate the skin even during prolonged contact.

Of course, the electrolyte must be of such a nature and composition that when in contact with the electrode it is electrically stable, i.e., it should provide good performance, such as low and stable offset voltages and low impedance throughout its use. It should not deteriorate, dry up or deleteriously affect the electrode. Nor should it be so viscous as to fail to adequately penetrate the skin. In short, storage stability or good shelf-like are very desirable.

Obviously, some very stringent requisites are being placed on body electrodes of the type contemplated herein. The search persists for improved electrode assemblies, as is evident from the following references which are deemed of interest: U.S. Pat. Nos. 3,027,333; 3,048,549; 3,170,459, 3,265,638; 3,420,223; 3,487,827; 3,567,657; 3,590,810; 3,607,788; "Principles of Applied Biomedical Instrumentation", by L. A. Geddes & L. E. Baker, 1968, pp. 208–9 and 243–245.

U.S. Application Ser. Nos. 11,208 and 103,498, now U.S. 3,701,346 patented Oct. 31, 1972, described in detail electrode assemblies of the type contemplated herein, particularly the latter application which is incorporated herein by reference and teaches a pre-filled electrode assembly essentially as shown in the drawing of the instant application.

It is the primary object of the present invention to provide a very unique and versatile electrode/electrolyte assembly having extremely desirable properties, included among which are a accuracy and reliable bioelectrical conductance.

THE INVENTION

The present invention relates to a novel body electrode and its use in sensing the bioelectrical potentials of a living animal body. More particularly the instant discovery concerns an electrode/electrolyte assembly wherein the electrode is made of stainless steel and the electrolyte is an aqueous alkali metal sulfate composition.

According to a more specific and preferred embodiment the electrolyte is an aqueous composition having an alkali metal sulfate concentration in the range, by weight, of about 1% upto about the saturation point of alkali metal sulfate in water. Preferably a small but effective amount of a water-soluble, water-swellable mucilage is present in the aqueous alkali metal sulfate solution to provide a viscous electrolytic mixture which, according to a still further embodiment, is absorbed by a sponge-like cellular matrix to provide a highly viscous semisolid electrolyte composition.

While a concentration of alkali metal sulfate in the range of about 1% to about the saturation point in water may be employed, a concentration in the range of about 10% to about 20%, by weight, is preferred.

Typical alkali sulfates within the purview of the present invention are the alkali metal sulfates, such as sodium, potassium and lithium sulfates.

Among the water-soluble, water-swellable mucilages (also known as gelling aids and water-soluble resins) useful herein are carboxymethylcellulose, polyvinyl alcohols, cellulosic gums, polymethylene oxide, sodium alginate, gum tragacanth, polyacrylic acids, such as those hydrophilic, high viscosity, polyacrylic acids having a molecular weight of about (1) million to about (6) million and useful in cosmetic and pharmaceutical preparations, e.g., the Carbopol water-soluble resins. (Carbopol is a trademark used by B. F. Goodrich Chemical Co.)

Best results are achieved with the polyacrylic acids by neutralizing same with any of a number of neutralizing agents, such as the fairly strong organic and inorganic bases, including but not limited to NaOH, KOH, $NH_4OH$, alkyl amines (mono-, di-, and tri-), alkanol amines (mono-, di-, and tri-), such as triethanolamine, triamylamine, dodecylamine, di(2-ethylhexyl)amine, and the like.

The resulting neutralized mucilage is usually present in the concentration of about 0.2% to about 8.0% preferably from about 0.85% to about 5.0%, by weight, based upon the total weight of the electrolyte composition.

If desired, conventional additives, such as mold inhibitors and the like, may be present in small quantities, usually less than about 1%. For example, very desirable results are achieved with chlorinated aromtic hydrocarbons, including 2-chloro-meta-5-xylenol, salts of organic acids, such as sodium benzoate, etc.

While the blending sequence of the electrolyte components admits of numerous variations, it is desirable and preferred to make the aqueous alkali metal sulfate solution separately and add thereto, with adequate stirring, the mucilage component which may then be neutralized in situ. The mold inhibitor or the like, if any, is preferably introduced with the neutralizing agent for more effective disbursement.

Generally, the electrolyte components are blended at ambient temperature and atmospheric pressure. If desired, for example, elevated temperatures and corresponding diminished pressure conditions, and vice versa (within the inherent tolerances and physical properties of the components) could be used very satisfactorily.

To better understand the present invention a preferred embodiment utilizing essentially the structure of U.S. application Ser. No. 103,498 heretofore alluded to and incorporated herein by reference will be described in some detail.

DESCRIPTION OF A PREFERRED EMBODIMENT

Figure 1:
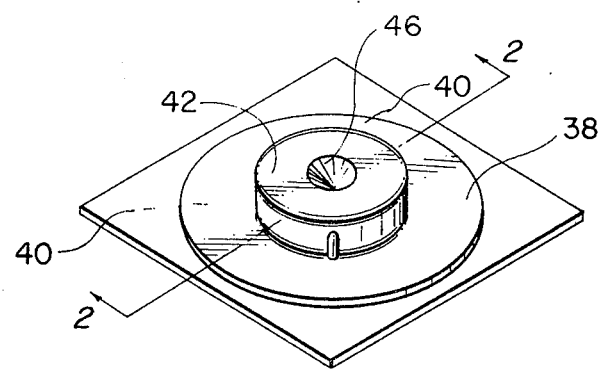
FIG. 1 is a perspective view of a protective covering for an electrode.

The drawing illustrates an electrode, generally designated 10, consisting of a circular flexible and resilient sheet 12 overlying a centrally located, inverted cup member 14 and sandwiched between a clamp plate 16 located on top of the sheet 12 which is of the same form and in alignment with the inverted cup member 14. The inverted cup member 14 is in the form of a cavity washer having a circular flat base with a semi-circular or U-shaped annular flange. The diameter of the cup member 14 is substantially greater than its height. These parts are held together by a metallic conductor formed from a male snap fastener member, generally designated 18, and which includes a lower, circular plate portion 20, from the center of which a hollow stud 22 projects upwardly, and an upper plate portion 24 having an upwardly protruding hollow socket portion 26 receiving the stud 22.

The parts are assembled and held together by centrally locating and aligning the cup member 14 and the clamp plate 16 on opposite sides of the sheet 12. The stud 22 is then inserted through aligned apertures in the centers of the sheet 12 and the members 14 and 16 and into the socket 26. The pressing together of the snap fastener portions causes the upper end of the stud 22 to fold inwardly and its side walls to collapse outwardly whereupon the snap fastener parts are tightly wedged together.

The bottom surface of the sheet 12 has a commercially available, medical grade acrylic pressure sensitive adhesive coating 28. Until the electrode 10 is to be used, the adhesive coating 28 is covered by a protective paper sheet 30 having a release coating on its face which engages the adhesive coating 28.

The sheet 12 is preferably formed of a foamed plastic, such as polyvinyl chloride, which provides for adequate aeration or ventilation of the skin. Such a sheet is quite flexible, readily conforming to skin contours and permitting free movement of the skin to which it is applied. The cup member 14 may be vacuum formed from a thermoplastic sheet material which is slightly flexible but sufficiently rigid to prevent its collapse. A variety of plastic materials may be used to form the cup member 14, examples being vinyl, linear polyethylene, and cellulose acetate butyrate.

The electrolyte is preassembled with the electrode 10 by soaking a disc-shaped sponge-like cellular matrix 32 of non-conductive, open-cell material with an electrode jelly. The sponge-like matrix 32 preferably has a diameter substantially equal to the diameter of the base of the cup member 14 and a thickness greater than the depth of the cup member 14. It is sufficiently heavily laden with electrode jelly that, when the electrode 10 is pressed on the skin, the jelly fills the entire volume of the cavity between the skin and the conductive plate portion 20 whereupon good electrical contact between the skin and the conductor plate portion 20 through the jelly is assured.

The sponge-like matrix 32 may be manufactured from open-cell polyurethane foam material although other cellular materials would be suitable. The sponge-like matrix 32 may be soaked with the jelly (e.g., sodium sulfate) by immersing it in a quantity of jelly, squeezing it under pressure and then gradually releasing the pressure before removing it from the jelly in the same manner that one would load a sponge with water. Of course it could be soaked with jelly by other methods.

Since wetted by the jelly, the soaked sponge-like matrix 32 tends to adhere to the conductive plate portion 20 and the base of the cup member 14. The adhesion is sufficient that the soaked sponge-like matrix 32 may simply be placed into position on the conductive plate portion 20 and the cup member 14 without the use of additional adhesives. When so placed, the electrode 10 is ready for use.

Figure 2:
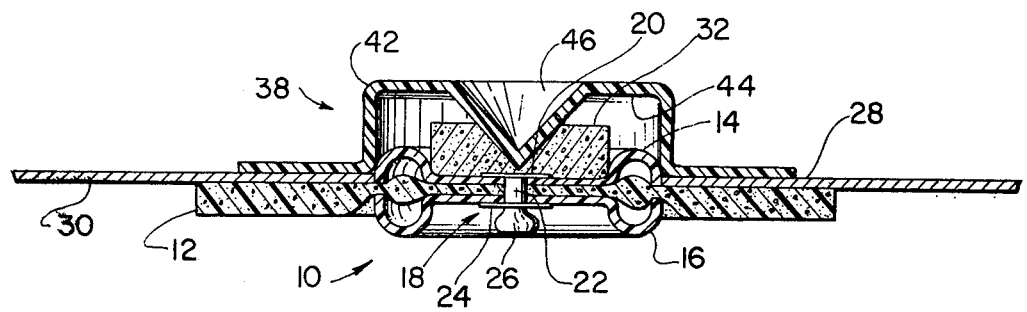
FIG. 2 is a cross sectional view of the electrode and protective covering taken along line 2–2 of FIG. 1.

Further in accordance with this invention, a protective cover 38 in FIGS. 1 and 2 is provided for the cup member 14 and the jelly soaked sponge-like matrix 32 so that the electrode 10 may be stored ready for immediate use. The cover 38 comprises an essentially flat strip of non-conductive plastic sheet having circular flat ends 40 and a raised center portion 42 formed as a cylinder, the inner diameter of which is substantially the same as the outer diameter of the cup member 14. The height of the cylindrical center portion 42 is greater than the combined height of the cup member 14 and the pad 32 whereupon the inside base surface, designated 44, of the center portion 42 is spaced from the pad 32. However, the base of the center portion 42 has a centrally located, inwardly directed conical projection 46, the lowermost end of which is spaced from the plane of the protective sheet 30 by considerably less than the thickness of the sponge-like matrix 32. For reasons discussed below, the projection 46 is so designed that, when the parts are assembled, the area of contact between the projection 46 and the sponge-like matrix 32 is considerably less than the combined area of contact between the sponge-like matrix 32 and the conductive plate portion 20 and the base of the cup member 14.

The cover 38 is assembled on the back face of the sheet 30 with the cylindrical center section 42 slipped over the cup member 14. The protective cover 38 serves not only to prevent soiling of the sponge-like matrix 32 but also, because the conical projection 46 engages the sponge-like matrix 32, it holds the sponge-like matrix 32 firmly in the cup member 14 and against the conductive plate portion 20. When the electrode 10 is to be used, the protective sheet 30 is merely peeled away from the sheet 12, taking with it the protective cover 38.

EXAMPLES

The present invention will best be understood from the following examples in which, unless otherwise indicated, percentages and parts are by weight.

Example I

The following components are blended into an electrolyte composition:
- 93.3 parts water
- 2.0 parts Carbopol* 940
- 1.6 parts triethanolamine
- 0.1 part 2-chloro-m-xylenol
- 3.0 parts sodium sulfate (anhydrous)

*Trademark used by B. F. Goodrich Chemical Co. for carboxypolymethylene (polyacrylic acid of 4-6 million molecular weight)

The anhydrous sodium sulfate is dissolved in water with mild stirring and the polyacrylic acid is then slowly sifted into the aqueous salt solution with rigorous stirring until the polyacrylic acid is homogeneously dispersed and/or dissolved. A solution of the triethanolamine and 2-chloro-m-xylenol, which is prepared by mild heating and stirring of the two components, is rapidly added to the mixture (with rigorous stirring and following the method used just above for polyacrylic acid). Rigorous stirring is continued for 10–60 minutes until the proper viscosity is obtained.

Example II

The following components are blended into an electrolyte composition:
- 79.1 parts water
- 2.4 parts Carbopol 940
- 3.0 parts triethanolamine
- 0.5 part 2-chloro-m-xylenol
- 15.0 parts sodium sulfate (anhydrous)

Blending is carried out essentially as in Example I, above, with the exception that 2-chloro-m-xylenol and triethanolamine are added (after the polyacrylic acid) separately and sequentially with vigorous stirring upon each addition.

Example III

The following components are blended into an electrolyte composition essentially as taught in Example I, above:
- 74.3 parts water
- 2.4 parts Carbopol 940
- 3.1 parts triethanolamine
- 0.2 part 2-chloro-m-xylenol
- 20.0 parts sodium sulfate (anhydrous)

Figure 3:
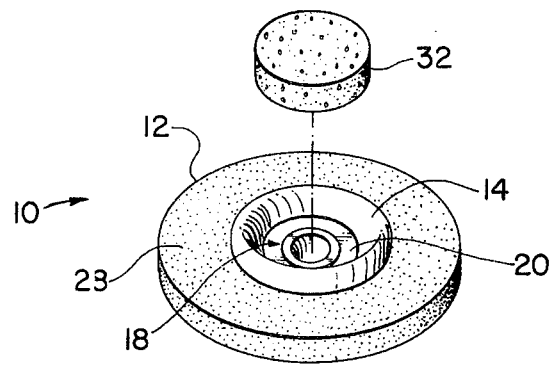
FIG. 3 is a partially exploded perspective view of the underside of the electrode with the protective covering removed.
Figure 3:
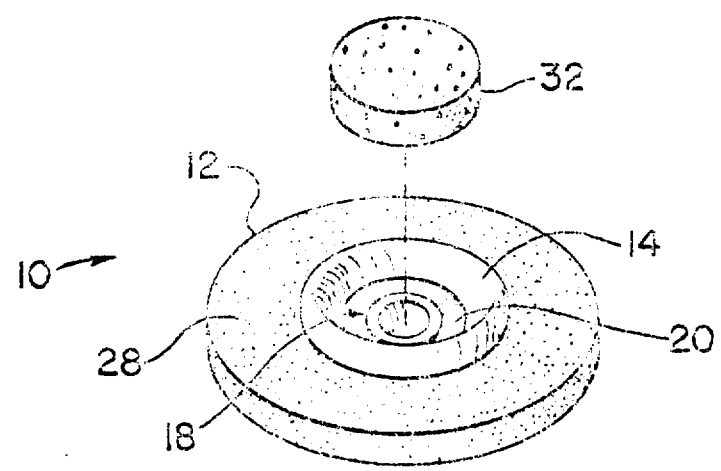

The electrolyte composition of each of the above examples exhibited the following very desirable properties when used to soak a sponge-like cellular flexible polyurethane matrix and the resulting semisolid composition tested by placing same in a body electrode of the type shown in FIGS. 1 to 3 of the drawing:

In the first place, electrodes thus prefilled did not - quite surprisingly corrode even after months and months; NaCl/stainless steel prefilled electrodes corroded in a matter of days, particularly those NaCl electrolytes having greater than isotonic concentrations of NaCl. Of course, any corrosion leads to very undesirable electrical artifacts.

The above examples also provide an electrode/electrolyte system which exhibits very low skin impedance, yet even after prolonged contact with the skin showed no dermatological effects.

Prior art emphatically and repeatedly points out that stainless steel is a poor choice of metal conductor to use in sensing bioelectric potentials. The art indicates that the use of stainless steel results in high, variable erratic offset potential causing distorted wave forms and base line drift in electrocardiographic and encephalographic monitoring, particularly with monitoring equipment of low input impedance. It has been found, pursuant to the present invention and quite surprisingly, that the stainless steel/alkali metal sulfate electrode system prepared as in the above examples and otherwise taught herein achieves not only lower but stable offset potentials, thus, resulting in a highly desirable bioelectrical sensing system.

Pursuant to statutory requirements, there are described above the invention and what are now considered its best embodiments. It should be understood, however, that the invention can be practiced otherwise then as specifically described, within the scope of the appended claims.

I claim:

1. In an electrode/electrolyte assembly for use in sensing the bioelectrical potentials of a living animal body and having means defining a cavity opening to the body and an electrode member at the base of the cavity and projecting therethrough, an electrolyte substantially filling said cavity and in direct contact with said electrode, and said electrode being adapted to be electrically connected to an external electrically responsive member, the improvement wherein the electrode is stainless steel and the electrolyte in said cavity means is an alkali metal surface.

2. The assembly of claim 1 wherein the electrolyte is an aqueous composition containing, by weight, from about 1% to about an aqueous saturated solution of alkali metal sulfate.

3. The assembly of claim 2 wherein the electrolyte is an aqueous composition containing, by weight, from about 10% to about 20% alkali metal sulfate.

4. The assembly of claim 2 wherein the alkali metal sulfate is sodium sulfate.

5. The assembly of claim 2 including a sponge-like cellular matrix wherein the electrolyte is an aqueous highly viscous semisolid composition comprising, by weight, from about 1% to about an aqueous saturated solution of alkali metal surface, and a small amount of a water-soluble, water swellable mucilage, said electrolyte being impedded in said sponge-like cellular matrix.

6. The assembly of claim 5 wherein the mucilage is a neutralized, water-soluble, waterswellable carboxypolymethylene present in the concentration of about 0.2% to about 5.0%, based upon the total weight of the electrolyte composition.

7. The assembly of claim 5 wherein the means defining a cavity opening of the body is a non-conductive cup member containing therein the aqueous highly viscous semisolid alkali metal sulfate electrolyte.

8. The assembly of claim 7 wherein the aqueous highly viscous semisolid electrolyte composition substantially fills the interior of said cup member and has a thickness at least as great as the depth of said cup member.

9. The assembly of claim 8 wherein the thickness of said aqueous highly viscous semisolid electrolyte composition exceeds the depth of said cup member.

10. The assembly of claim 9 wherein a removable protective covering overlies the open end of the cup member, said covering being a sheet material having a raised portion overlying the semisolid electrolyte protruding from the cup member, said raised portion being spaced from said semisolid electrolyte but for a projection engaging the protruding end of said semisolid electrolyte for holding the semisolid electrolyte in said cup member.

11. The assembly of claim 10 wherein an aperatured flexible and resilient sheet surrounds the generally centrally located cup member and overlies the exterior of the closed base end thereof, the surface of said flexible and resilient sheet in coplanar relationship to the open end of the cup member having a pressure sensitive adhesive coating thereon for adhering to a body surface, and means for securing said flexible, resilient sheet to said cup member including the stainless steel electrode which projects through the base of the cup member and through said aperature in said flexible and resilient sheet.

12. The assembly of claim 11 wherein the electrode projecting through the base of said cup member base and the aperture in said flexible, resilient sheet is a conductive metal snap fastener, that portion of which in contact with the electrolyte is stainless steel.

* * * * *

UNITED STATES PATENT OFFICE
CERTIFICATE OF CORRECTION

PATENT NO. : 3,946,730
DATED : March 30, 1976
INVENTOR(S) : Robert Paul Monter

It is certified that error appears in the above-identified patent and that said Letters Patent are hereby corrected as shown below:

In the drawing, Figure 3, change reference numeral "23" to --28--, as shown on the attached sheet.

Column 1, line 44, change "shelf-like" to --shelf-life--.

Column 5, line 13, change "sall" to --salt--.

Column 6, line 28, change "surface" to --sulfate--.

Column 6, line 42, change "surface" to --sulfate--.

Column 7, line 3, change "aperatured" to --apertured--.

Column 8, line 3, change "aperature" to --aperture--.

Signed and Sealed this

Fourteenth Day of September 1976

[SEAL]

Attest:

RUTH C. MASON
Attesting Officer

C. MARSHALL DANN
Commissioner of Patents and Trademarks